US00PP10926P

United States Patent [19]

Bradford et al.

[11] Patent Number: Plant 10,926

[45] Date of Patent: Jun. 1, 1999

[54] NECTARINE TREE NAMED 'AUGUST PEARL'

[76] Inventors: Lowell Glen Bradford, 12439 E. Savana Rd.; Norman G. Bradford, 11875 E. Savana Rd., both of Le Grand, Calif. 95333

[21] Appl. No.: 08/982,137

[22] Filed: Dec. 1, 1997

[51] Int. Cl.[6] ..... A01H 5/00

[52] U.S. Cl. ..... Plt./188

[58] Field of Search ..... Plt./40.1, 41.1, Plt./42.1, 188

[56] References Cited

U.S. PATENT DOCUMENTS

P.P. 7,193 3/1990 Bradford et al. ..... Plt./41

P.P. 8,947 10/1994 Bradford et al. ..... Plt./40.1

*Primary Examiner*—Howard J. Locker

*Assistant Examiner*—Ashwin Mehta

[57] ABSTRACT

The present invention relates to a nectarine tree, *Prunus persica*, and more particularly to a new and distinct variety broadly characterized by a large size, vigorous, self-fertile, productive and regular bearing tree. The fruit matures under the ecological conditions described in the middle of August, with first picking on August 9, 1997. The fruit is uniformly large in size, subacidic and sweet in flavor, white in flesh color, globose in shape, clingstone in type, very firm in texture, and nearly full red in skin color. The variety was a first generation cross using 'Red Glen' (U.S. Plant Pat. No. 7,193) yellow flesh nectarine as the selected seed parent and 'August Snow' (U.S. Plant Pat. No. 8,947) white flesh nectarine as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as 'August Pearl'. The present variety was developed by us in 1993 in a cultivated area of our experimental orchard at Bradford Farms near Le Grand, Calif. in Merced County (San Joaquin Valley). It was a first generation cross using Red Glen (U.S. Plant Pat. No. 7,193) yellow flesh nectarine as the selected seed parent and 'August Snow' (U.S. Plant Pat. No. 8,947) white flesh nectarine as the selected pollen parent. Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The fruit produced by the present variety is most similar to its pollen parent, the 'August Snow' (U.S. Plant Pat. No. 8,947), by producing white flesh nectarines that are subacidic in flavor and harvest during August, but is distinguished therefrom and an improvement thereon by producing fruit that ripens about twelve days later, that is sweeter in flavor, that is clingstone instead of freestone, and that does not have a protruding tip at the apex.

The present variety is similar to its seed parent, 'Red Glen' (U.S. Plant Pat. No. 7,193), by producing nectarines that are large sized, clingstone, very firm, and full red in skin color, but is very distinguished by producing fruit that is white flesh instead of yellow flesh and that is subacidic in flavor instead of acidic.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard ripe on Aug. 14, 1997. All major color code designations are by reference to the Inter-Society Color Council, National Bureau of Standards. Common color names are also used occasionally.

Tree

Size: Large, surpassing a height of 9' [2.74 meters] during the third growing season after typical dormant pruning.

Vigor: Vigorous, responding typically to irrigation and fertilization.

Growth: Upright and dense.

Form: Vase formed.

Hardiness: Hardy, able to survive typical winter weather experienced in central California.

Production: Productive, thinning necessary.

Fertility: Self-fertile.

Bearing: Regular bearer, with no alternate bearing yet observed.

Trunk:

- *Size.*—Medium, reaching a diameter of 3.5" [88.9 mm] during the third growing season.
- *Texture.*—Medium rough, with roughness increasing with age.
- *Bark color.*—Grayish yellowish brown [80. gy.yBr].
- *Lenticels.*—Numerous. Color: Moderate orange yellow [71. m.OY]. Average size: ⅛" to ⅜" [3.2–9.5 mm.].

Branches:

- *Size.*—Medium, typical of the species.
- *Texture.*—Smooth on 1st year wood, increasing roughness with age.

*Color.*—1st year wood topside: Grayish red [19. gy.R]. 1st year wood underside: Moderate yellow green [120. m.YG]. Older wood: Moderate brown [58. m.Br].

*Lenticles.*—Numerous, small. Color: Deep orange yellow [69. deep OY]. Average size: 1/16" [1.6 mm.].

Leaves:

*Size.*—Medium. Average length: 5¾" [146.1 mm.]. Average width: 1¼" [31.8 mm.].

*Thickness.*—Medium.

*Form.*—Elliptical.

*Apex.*—Acuminate.

*Base.*—Acute.

*Surface.*—Smooth.

*Color.*—Dorsal surface: Moderate olive green [125. m.OlG]. Ventral surface: Moderate yellow green [120. m.YG].

*Margin.*—Finely serrate.

*Venation.*—Pinnately net veined.

*Petiole.*—Average length: ½" [12.7 mm.]. Average thickness: 1/16" [1.6 mm.]. Color: Moderate yellow green [120. m.YG].

*Stipules.*—Numerous. Average length: ⅜" [9.5 mm.].

*Glands.*—Numbers: 4 to 6 per leaf. Position: Alternately positioned on petiole and base of blade. Size: Small. Form: Globose. Color: Moderate greenish yellow [102. m.gY].

Flower buds:

*Hardiness.*—Hardy, with respect to central California winters.

*Diameter.*—Typically ⅜" [9.5 mm] 1 week before bloom.

*Length.*—Typically ¾" [19.1 mm] 1 week before bloom.

*Form.*—Free.

*Surface.*—Pubescent.

Flowers:

*Blooming period.*—Medium as compared with other varieties.

*Onset of bloom.*—One percent on Feb. 27th , 1997.

*Type.*—Showy.

*Average diameter.*—1¾" [44.45 mm].

*Color.*—Pale purplish pink [252. p.pPK].

Fruit

Maturity when described: Hard ripe, Aug. 14, 1997.

Date of first picking: Aug. 9, 1997.

Date of last picking: Aug. 21, 1997.

Size: Uniform, large.

*Average diameter axially.*—2⅝" [66.7 mm.].

*Average transversely in suture plane.*—2⅝" [66.7 mm.].

*Typical weight.*—6.06 ounces [172 grams].

Form: Globose, uniform, symmetrical.

*Longitudinal section form.*—Round.

*Transverse section through diameter.*—Round.

Suture: An inconspicuous line that transforms into a sharp groove very close to the stem and a shallow groove toward the apex, having a slight depression beyond the pistil point.

Ventral surface: Rounded, lipped toward this apex, usually more on one side.

Lips: Slightly unequal.

Cavity: Flaring, circular, suture showing on one side with stem marks typical.

*Depth.*—⅝" [15.9 mm.].

*Breadth.*—1" [25.4 mm.].

Base: Rounded to truncate.

Apex: Rounded.

Pistil point: Negligible in length, depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed.

*Color.*—Dark red [16. d.R] over a moderate pink [5. m.Pk] background, with a slight amount of light orange [52. l.O] freckling toward the apex.

Flesh:

*Color.*—Yellowish white [92. y.White] with dark red [16. d.R] streaking extending about ⅜" [9.5 mm] from the stone.

*Amygdalin.*—Scarce.

*Juice.*—Abundant, rich.

*Texture.*—Very firm, very crisp.

*Fibers.*—Abundant, fine.

*Ripens.*—Slightly earlier at the apex.

*Flavor.*—Subacidic and sweet, averaging 18 brix.

*Aroma.*—Slight.

*Eating quality.*—Excellent.

Stone

Type: Clingstone.

Form: Oval.

Base: Straight.

Apex: Very acute.

Sides: Equal.

Surface: Irregularly furrowed toward the apex, pitted toward the base.

Ridges: Jagged toward the base.

Color: Moderate yellowish brown [77. m.yBr].

Pit wall: ¼" [6.4 mm.] thick.

Tendency to split: None observed.

Kernel:

*Form.*—Oval.

*Taste.*—Sweet.

*Viable.*—Yes.

*Average width.*—½" [12.7 mm.].

*Average length.*—11/16" [17.5 mm.].

*Skin color.*—Strong brown [55. s.Br] when dry.

*Pellicle color.*—Dark grayish yellowish brown [81. d.gy.yBr].

*Amygdalin.*—Scant.

Use

Market: Fresh and long distance shipping.

Keeping quality: Fruit quality observed to remain in good condition in excess of 14 days in cold room at 36° Fahrenheit [2° Celsius].

Resistance to insects: No unusual susceptibilities noted.

Resistance to diseases: No unusual susceptibilities noted.

Although the new variety of nectarine tree possesses the described characteristics under the ecological condtions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its pollen parent, the 'August Snow' (U.S. Plant Pat. No. 8,947), by producing white flesh nectarines that are subacidic in flavor and harvest during August, but is distinguished therefrom and an improvement thereon by producing fruit that ripens about twelve days later, that is sweeter in flavor, that is clingstone instead of freestone, and that does not have a protruding tip at the apex.

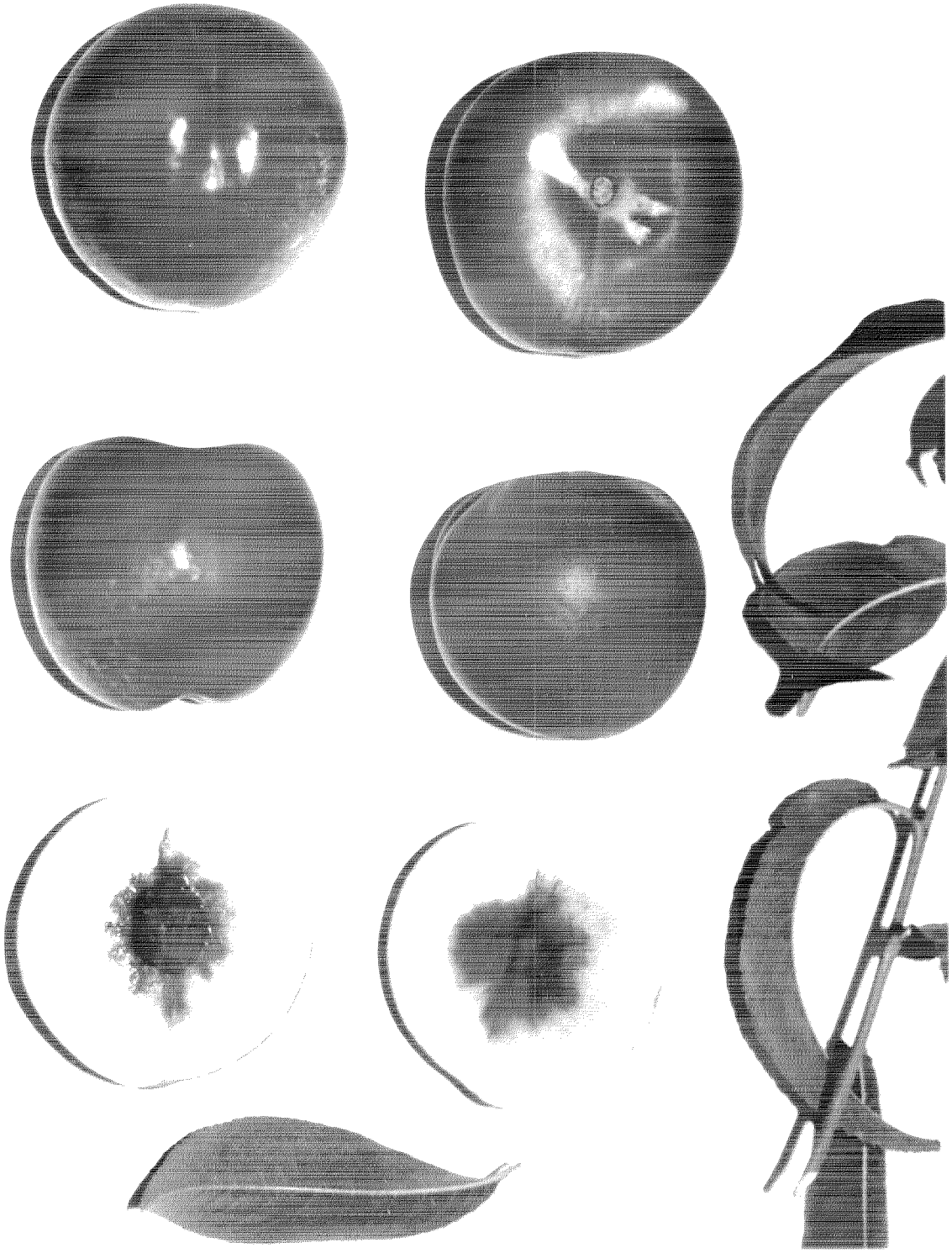

* * * * *